(12) United States Patent
Vulcu et al.

(10) Patent No.: US 12,115,263 B2
(45) Date of Patent: Oct. 15, 2024

(54) PROCESS AND APPARATUS FOR KILLING SKIN OR TISSUE SURFACE BACTERIA

(71) Applicants: Emil Vulcu, Columbia, MD (US); Bianca Marie Makris, Huntingdon Valley, PA (US)

(72) Inventors: Emil Vulcu, Columbia, MD (US); Bianca Marie Makris, Huntingdon Valley, PA (US)

( * ) Notice: Subject to any disclaimer, the term of this patent is extended or adjusted under 35 U.S.C. 154(b) by 751 days.

(21) Appl. No.: 17/183,318

(22) Filed: Feb. 23, 2021

(65) Prior Publication Data
US 2021/0275699 A1 Sep. 9, 2021

Related U.S. Application Data

(60) Provisional application No. 63/100,258, filed on Mar. 5, 2020.

(51) Int. Cl.
 *A61L 2/00* (2006.01)
 *A61L 2/26* (2006.01)
 *A61N 1/18* (2006.01)

(52) U.S. Cl.
 CPC .............. *A61L 2/0011* (2013.01); *A61L 2/26* (2013.01); *A61N 1/18* (2013.01)

(58) Field of Classification Search
 CPC . A61L 2/0011; A61L 2/26; A61L 2/03; A61N 1/18; A61C 19/06
 See application file for complete search history.

(56) References Cited

U.S. PATENT DOCUMENTS

| | | | | |
|---|---|---|---|---|
| 2,121,875 A | * | 6/1938 | Kruse | A61L 2/238 433/32 |
| 3,763,850 A | * | 10/1973 | Gaudebout | A61B 5/1473 600/360 |
| 4,244,373 A | * | 1/1981 | Nachman | A61N 1/36034 607/9 |
| 4,854,865 A | * | 8/1989 | Beard | A61C 7/00 433/18 |
| 5,336,570 A | * | 8/1994 | Dodge, Jr. | H01M 8/242 429/513 |
| 6,584,349 B1 | * | 6/2003 | Sage, Jr. | A61N 1/0444 604/20 |
| 8,221,396 B2 | | 7/2012 | Dehnad et al. | |
| 8,771,323 B2 | | 7/2014 | Dehnad et al. | |
| 8,927,004 B1 | | 1/2015 | Dehnad et al. | |
| 8,999,367 B1 | | 4/2015 | Dehnad et al. | |
| 9,108,051 B2 | | 8/2015 | Dehnad et al. | |
| 9,248,254 B2 | | 2/2016 | Dehnad et al. | |
| 9,452,242 B2 | | 9/2016 | Dehnad et al. | |
| 9,789,298 B2 | | 10/2017 | Dehnad et al. | |
| 9,821,094 B2 | | 11/2017 | Dehnad et al. | |
| 9,889,284 B2 | | 2/2018 | Dehnad et al. | |

(Continued)

FOREIGN PATENT DOCUMENTS

| | | | | |
|---|---|---|---|---|
| EP | 1187236 A2 | * | 3/2002 | ......... H01M 2/0222 |
| WO | WO-2007003003 A1 | * | 1/2007 | ............. C02F 1/463 |

*Primary Examiner* — Regina M Yoo
(74) *Attorney, Agent, or Firm* — PAUL & PAUL

(57) ABSTRACT

A device for killing bacteria on a surface includes an application anode plate having a silver surface adapted for contact with a first epithelial surface, a cathode plate having an electrically conductive cathodic surface layer adapted for contact of the surface layer with a second epithelial surface; and a source of direct electrical current.

15 Claims, 2 Drawing Sheets

(56) References Cited

U.S. PATENT DOCUMENTS

| | | |
|---|---|---|
| 10,004,548 B2 | 6/2018 | Dehnad et al. |
| 10,265,435 B2 | 4/2019 | Dehnad et al. |
| 10,368,929 B2 | 8/2019 | Dehnad et al. |
| 2005/0120621 A1* | 6/2005 | Lawson ................... C10L 1/026 44/388 |
| 2005/0275330 A1* | 12/2005 | Sung ...................... H10N 15/00 313/311 |
| 2006/0227523 A1* | 10/2006 | Pennaz ............... H01M 10/425 257/679 |
| 2006/0286448 A1* | 12/2006 | Snyder .................. H01M 4/139 29/623.5 |
| 2013/0041238 A1* | 2/2013 | Joseph ................. A61L 29/041 600/323 |

\* cited by examiner

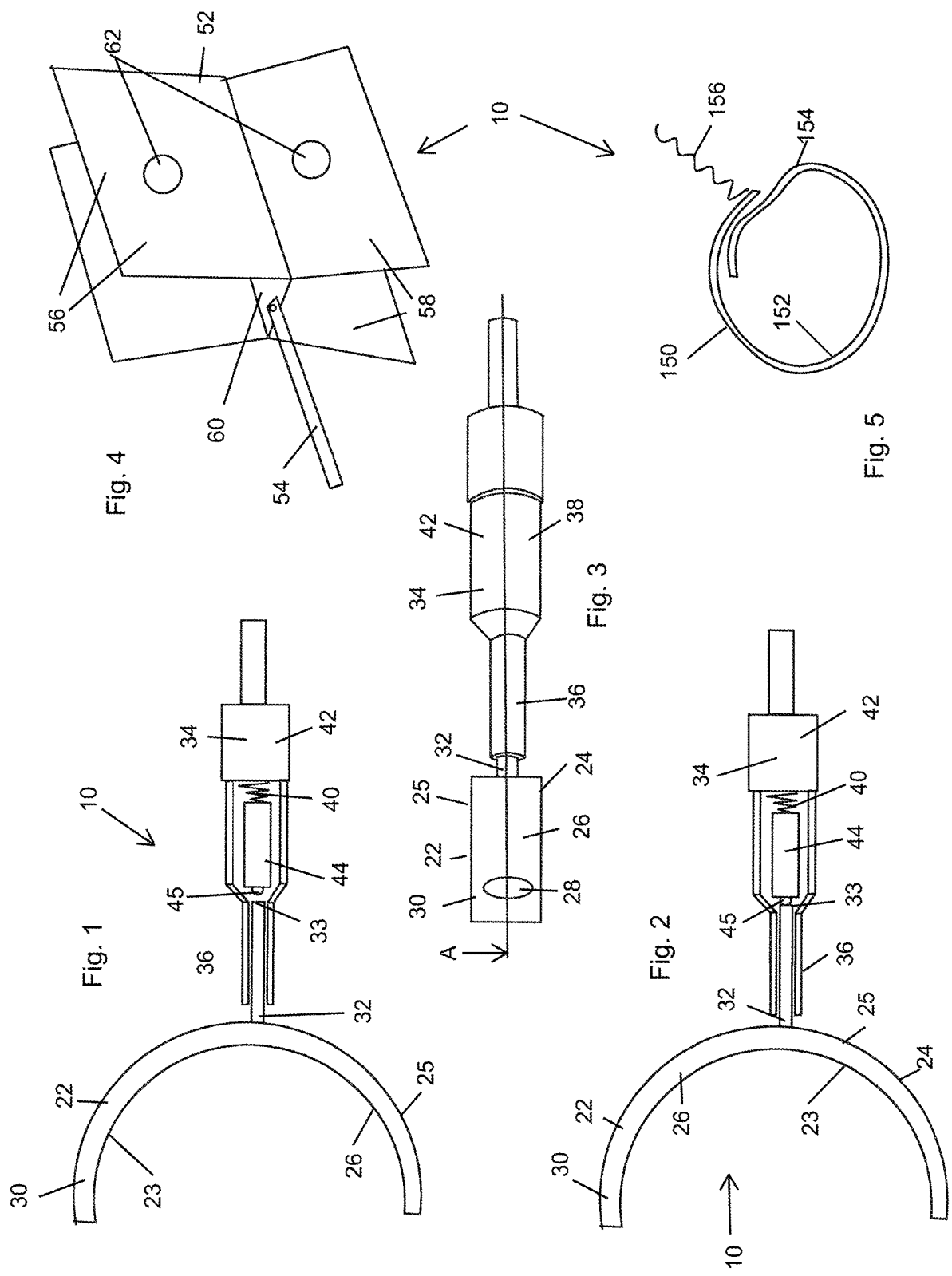

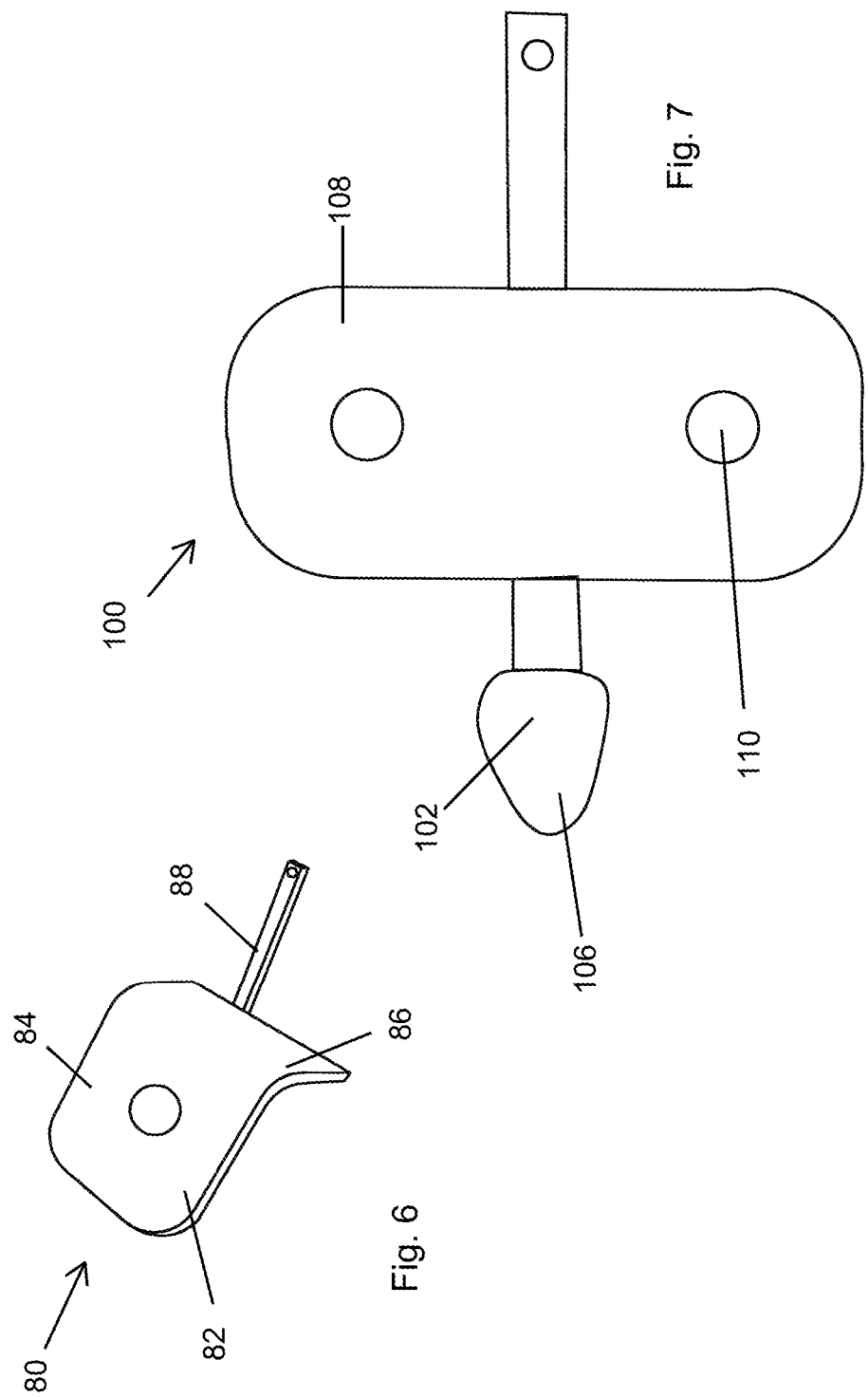

PROCESS AND APPARATUS FOR KILLING SKIN OR TISSUE SURFACE BACTERIA

CROSS-REFERENCE TO RELATED APPLICATION

The present application claims the priority of U.S. Provisional Patent Application No. 63/100,258, filed Mar. 5, 2020, which is incorporated herein by reference.

BACKGROUND OF THE INVENTION

1. Field of the Invention

The present invention relates to the bactericidal treatment of skin and tissue surfaces.

2. Brief Description of the Prior Art

It is known that silver ions can kill or neutralize bacteria.

Examples of the use of silver ions for their bactericidal efficacy are disclosed, for example, in U.S. Pat. Nos. 10,368,929, 10,265,435, 10,004,548, 9,889,284, 9,821,094, 9,789,298, 9,452,242, 9,248,254, 9,108,051, and 8,999,367, each incorporated herein by reference.

Silver ions can be produced electrochemically in an aqueous environment if a silver part is connected to the anode (+) of a DC electrical power supply or battery and both anode and cathode are immersed in the aqueous environment.

The silver ions can be also produced by a galvanic cell in a wet environment when the silver is the anode (+) and a dissimilar metal from the galvanic table for electrical potential is the cathode (−) and they both being in a close mechanical/electrical contact with each other. If the electrical potential between anode and cathode is more than one volt the silver anode will produce silver ions continuously and unlimited in a watery environment similar to a battery until one of the metal is completely consumed due to oxidization.

There is a continuing need for efficacious devices and processes for the treatment of harmful bacteria on a variety of surfaces.

SUMMARY OF THE INVENTION

The present invention provides a device and a process for killing bacteria on a surface, such as on human skin or the surface of a layer of tissue. The device includes an application anode plate having a silver surface. The application plate is adapted for contact with, or for being positioned in proximity to, a surface, such as a first epithelial surface. The device includes an application cathode plate having an electrically conductive cathodic surface layer. The cathode plate is adapted for contact with, or being positioned in close proximity to, a second epithelial surface. The device also includes a source of direct electrical current adapted to provide an electrical potential between the silver surface and the cathodic surface layer sufficient to provide an electric current. The application anode plate and the cathode plate are optionally in electrical communication with the source of direct electrical current, such as a battery or power supply. In one aspect of the present invention, the anode plate has a silver-plated surface. In another aspect, the cathode plate includes a flexible base. Preferably, the invention further includes a metallic layer in contact with the silver surface, and the metallic layer has a higher reduction potential than silver. In a presently preferred aspect of the invention, the metallic layer is magnesium.

In a first embodiment of the present invention, the application anode plate is formed into a generally "U"-shape adapted to be received within a human mouth adjacent the teeth and gums. Preferably, in this embodiment, the application plate includes a stem to form an anode, the stem protruding outwardly from the center (or from the side) of the application plate and including an electrically conductive interior portion and an electrically insulating exterior portion. In this embodiment, the device further includes an electrically conductive shell receiving the stem over the electrically insulating exterior portion of the stem, where the shell being adapted to be contacted by the lips of the mouth, and the shell includes the cathodic surface layer. Preferably, the shell is movable from a first position in which the application plate is electrically insulated from the source of electric current and a second position in which the application plate is in electrical communication with the source of electric current. Preferably, the shell is biased towards the first position.

In a second embodiment of the present invention, the application anode plate is formed into a generally "H"-shape adapted to be received within the human mouth adjacent the teeth and gums.

In a third embodiment of the present invention, the application anode plate is formed into a first section and a second section generally perpendicular to the first section adapted to be received within the human mouth between the lips.

In a fourth embodiment of the present invention, the application anode plate includes a generally flat first section and a generally bulbous second section adapted to be inserted within the human anus.

Preferably, in a device of the present invention the reduction potential between the silver surface and the cathodic surface layer is positive.

Preferably, a device of the present invention further includes a metallic layer in contact with the silver surface, with the metallic layer having a higher reduction potential than silver. Preferably, the metallic layer is magnesium.

The present invention also provides a process for sanitizing an epithelial surface. The process includes providing an application anode plate having a silver surface, the application plate being adapted for contact with a first epithelial surface, The process also includes providing a cathode plate having an electrically conductive cathodic surface layer, the cathode plate being adapted for contact of the surface layer with a second epithelial surface. Further, the process also includes providing a source of direct electrical current adapted to provide an electrical potential between the silver surface and the cathodic surface layer sufficient to provide an electric current. The process also includes placing the application anode plate and the cathode plate optionally in electrical communication with the source of direct electrical current such that silver ions are formed on the surface of the silver surface.

BRIEF DESCRIPTION OF THE DRAWINGS

FIG. 1 is a schematic plan sectional view of a first embodiment of the device of the present invention being shown in a first or "off" position.

FIG. 2 is a schematic plan sectional view of the device of FIG. 1 being shown in a second or "off" position.

FIG. 3 is a side elevational view of the device of FIG. 1.

FIG. 4 is a schematic perspective view of the anode of a second embodiment of the device of the present invention.

FIG. 5 is a top plan view of a cathode of the device of a second embodiment of the present invention.

FIG. 6 is a schematic perspective view of the anode of a third embodiment of the device of the present invention.

FIG. 7 is a side view of the anode of a fourth embodiment of the device of the present invention.

DETAILED DESCRIPTION

In one aspect, the present invention provides a device that preferably includes a silver (99.9% w/w) metal plate or the like, which serves as an anode (+), connected through a flexible electrical conductive wire to the anode of a source of DC current, such as a battery or a power supply, and a metallic, electrically conductive, cathode plate connected to the cathode of the source of DC current.

In use, the silver anode is connected/attached/strapped to a human or animal skin or tissue to be treated, and the cathode conductive plate is connected/strapped to a healthy skin tissue at a limb site to close the electrical conductive circuit. Silver ions are produced at the silver anode for application to the skin or tissue area.

FIG. 1 provides a plan sectional view of a first embodiment of the device 10 of the present invention, taken along the line A-A of the side elevational view of FIG. 3. In this case, the application anode plate 20 is formed into a generally "U"-shape adapted to be received within a human mouth adjacent the teeth and/or gums. Preferably, in this embodiment, the application anode plate 20 includes a stem 32 to form an anode 30. The stem 32 preferably protrudes outwardly from the center of the application anode plate 20. Depending on whether the inside or the outside of the teeth or gums are to be treated, the anode stem 32 can preferably extend from the center of the outward face 26 of the application anode plate 20 so that the inner face 23 of the application plate 20 can be positioned adjacent the outside of the teeth and gums. If the inside of the teeth or gums are to be treated, the anode stem 32 can be affixed to the upper or lower edge 24 of the application anode plate 20, so that the outer face 26 of the application anode plate 20 can be positioned adjacent the inside of the teeth and gums (not shown).

The application plates of the present invention, including the application anode plate 20 of the first embodiment, are preferably formed from a material that will supply silver ions under an applied electrical potential, For example, the application anode plate 20 can be formed from silver, such as 99.5% silver, or a silver alloy, or may include only a thin layer or coating of metallic silver applied over and bonded to an underlying base 22 which can provide electrical conductivity. Alternatively, particles of metallic silver may be embedded in an electrically conductive base material, such as an electrically conductive thermoplastic or thermosetting synthetic plastic material. Alternatively, the base 22 may include electrically conductive structures as members of the conductive circuit. The application plate can be completely or only partially coated or otherwise constructed to provide silver ions, such that only specific portions of the surface of the application plate which lie in close proximity to the portions of the body of the user to be treated are adapted to release silver ions. For example, only the outward extending portions in close proximity to the gums can be adapted to supply silver ions for treatment of the gums.

The anode 30 can include a sacrificial metallic layer 28, formed from a material such as magnesium, mechanically attached to the inner or outer faces 23, 26 of the application anode plate 20 to reduce oxidation of the silver.

Preferably, the conformation of the base can be adjusted to closely conform to the surfaces of the teeth being treated. For example, the base can be formed from a material that softens as its temperature is increased, so that the base 22 can be molded to conform to or approximate the surfaces of the teeth being treated.

The first embodiment of the device 10 also includes a battery housing 34 having a stem section 36 extending coaxially from a battery section 38 and a handle 42. The inside diameter of the stem section 36 is sized to receive the stem 32 of the anode 30, and the relative lengths of the stem 32 of the anode 30 and the stem section 36 of the battery housing 34 are selected such that the tip of the stem 32 can contact the anode of a battery 44 retained inside the battery housing 34. A spring 40 is provided to urge the battery 44 towards the stem section 36. The exterior surface, other than the tip 33, of the stem 32 is provided with an electrically insulative material, such that the portion of the stem 32 received within the stem section 36 of the battery housing 34 is electrically isolated from the battery housing 34, and such that the exterior surface of the stem 32 includes an electrically conductive interior portion and an electrically insulating exterior portion.

In this embodiment, the stem section 36 forms an electrically conductive shell receiving the stem 32 over the electrically insulating exterior portion of the stem 32. Alternatively, the interior of the stem section 36 can be covered with a layer of an electrically insulative material and the insulation omitted from the stem 32, or both the interior of the stem section 36 and the exterior of the stem 32 can be covered with electrically insulative material.

The stem section or shell 36 is adapted to be contacted by the lips of the mouth. The stem section 36 includes the cathodic surface layer. Preferably, the battery housing 34, and thus the stem section 36, is movable from a first position in which the application plate is electrically insulated from the source of electric current, such as shown in FIG. 1, and a second position in which the application plate is in electrical communication with the source of electric current, such as shown in FIG. 2. Preferably, the battery housing 34 and hence the stem section 36 are biased towards the first position.

In operation, a user places her or his lips around the stem section 36 and pushes the battery housing 34 inward, until the battery's electrode 45 contacts the tip 33 of the stem 32, thus completing the electric circuit and permitting silver ions to be discharged from the anode 30. The contact of the tip 33 with the electrode 45 prevents the stem section 36 of the battery housing 34 from contacting the anode 30, and thus electrically isolating the two.

FIGS. 4 and 5 collectively portray a second embodiment 50 of the device of the present invention intended for use for treating opposing teeth and gums simultaneously on either side of the teeth. The device 50 includes an "H"-shaped anode plate 52 and a rod-shaped anode contact strip 54, which is preferably rotatably affixed to the anode plate 52 such that the orientation of the contact strip 54 can be adjusted to comfortably protrude from the mouth of a user when anode plate 52 is positioned in the mouth. The anode plate 52 is formed from a pair of spaced upwardly-extending upper plates 56 extending from parallel sides of a base plate 60, and a pair of spaced downwardly-extending lower plates 58 extending from the parallel sides of the base plate 60. The upper plates 56 and base plate 60 thus form an upper channel and the lower plates 58 and the base plate 60 thus form a lower channel. The anode plate 52 can also include a sacrificial metallic layer 62. In use, the anode plate 52 is positioned within the mouth of a user such that a portion of the upper row of teeth lie within the upper channel of the anode plate 52 and the lower row of the teeth lie within the lower channel of the anode plate 52.

The second embodiment also includes a cathode plate 150 (FIG. 5) preferably formed from a deformable material such that the cathode plate 150 can be positioned on a limb of a user proximate the anode plate 52 such that an electrical potential can be through the user's skin between the cathode plate 150 and the anode plate 52. The cathode plate 150 can be formed of an electrically conductive deformable spring-like material such as spring steel or the like, or include a base 154 formed from a synthetic polymeric material being provided with an electrically conductive surface layer 152. An electrically conductive connection 156 such as a conventional wire is provided to connect the cathode plate 150 to a source of electrical current such as a battery or other source of direct current. An electrically conductive cream can be applied to the user's skin in the area in which the cathode plate 150 is to be positioned.

In a third embodiment 80 of the device of the present invention, shown in perspective view of FIG. 6, a generally "J"-shaped anode plate 82 having a generally horizontally-extending first plate 84 and a generally vertically-extending second plate 86, with an electrically conductive contact strip 88 extending from the second plate 86 for connecting the anode plate 82 to a source of direct current. In this third embodiment 80, the cathode plate 150 of FIG. 5 can be employed in conjunction with the anode plate 82. In this case, the anode plate 82 is positioned between the lips of a user to be treated for proving treatment to the lips.

In a fourth embodiment 100 of the device of the present invention, shown in the side elevational view of FIG. 7, the anode plate 102 includes a generally bulbous interior element 106 shaped to be positioned within the anus of a user, the interior element being optionally connected by a rod-like stem section 104 to a generally planar exterior plate 108 which is positioned between the gluteal cheeks of the user. In this fourth embodiment 100, the cathode plate 150 of FIG. 5 can be employed in conjunction with the anode plate 102. Depending on the treatment desired, the surface of the interior element 106 and/or the surface of the exterior plate 108 can be silver, or otherwise provide silver ions to the area to be treated.

Various modifications can be made in the details of the various embodiments of the articles and method of the present invention, all within the scope and spirit of the invention as defined by the appended claims.

The invention claimed is:

1. A device for killing bacteria on a surface, the device including:
    an application anode plate having a silver surface, the application anode plate being adapted for contact with a first epithelial surface;
    a cathode plate having an electrically conductive cathodic surface layer, the cathode plate being adapted for contact of the electrically conductive cathodic surface layer with a second epithelial surface; and
    a source of direct electrical current adapted to provide an electrical potential between the silver surface and the electrically conductive cathodic surface layer sufficient to provide an electrical current;
    wherein the application anode plate and the cathode plate are optionally in electrical communication with the source of direct electrical current, and
    wherein the application anode plate is formed into a generally "U"-shape adapted to be received within a human mouth adjacent the teeth.

2. The device according to claim 1 wherein the application anode plate has a silver-plated surface.

3. The device according to claim 1 wherein the cathode plate includes a flexible base.

4. The device according to claim 1 further including a metallic layer in contact with the silver surface, the metallic layer having a higher reduction potential than silver.

5. The device according to claim 4 wherein the metallic layer is magnesium.

6. The device according to claim 1 wherein the application anode plate includes a stem to form an anode, the application anode plate having a center and a side, the stem protruding outwardly from the center or from the side of the application anode plate and including an electrically conductive interior portion and an electrically insulating exterior portion.

7. The device according to claim 6 further including an electrically conductive shell receiving the stem over the electrically insulating exterior portion of the stem, the electrically conductive shell being adapted to be contacted by the lips of the human mouth, the electrically conductive shell including the electrically conductive cathodic surface layer.

8. The device according to claim 7 wherein the electrically conductive shell is movable from a first position in which the application anode plate is electrically insulated from the source of direct electrical current and a second position in which the application anode plate is in electrical communication with a source of electrical current.

9. The device according to claim 8 wherein the electrically conductive shell is biased towards the first position.

10. A device for sanitizing a human mouth having lips, gums, and teeth, the device including:
    an application anode plate having a silver surface, the application anode plate being formed into a generally "U"-shape adapted to be received within the human mouth adjacent the gums and teeth, the application anode plate including a stem to form an anode, the stem protruding conductive interior portion and an electrically insulating exterior portion;
    an electrically conductive shell receiving the stem over the electrically insulating exterior portion, the electrically conductive shell being adapted to be contacted by the lips of the human mouth, the electrically conductive shell including a cathodic surface layer;
    a source of direct electrical current adapted to provide an electrical potential between the silver surface and the cathodic surface layer sufficient to provide an electrical current,
    wherein the application anode plate and the cathodic surface layer are optionally in electrical communication with the source of direct electrical current.

11. The device according to claim 10 wherein the electrically conductive shell is movable from a first position in which the application anode plate is electrically insulated from the source of direct electric current and a second position in which the application anode plate is in direct electrical communication with the source of direct electrical current.

12. The device according to claim 11 wherein the electrically conductive shell is biased towards the first position.

13. The device according to claim 10 wherein there is a reduction potential between the silver surface and the cathodic surface layer, and the reduction potential between the silver surface and the cathodic surface layer is positive.

14. The device according to claim 10 further including a metallic layer in contact with the silver surface, the metallic layer having a higher reduction potential than silver.

15. The device according to claim 14 wherein the metallic layer is magnesium.

* * * * *

UNITED STATES PATENT AND TRADEMARK OFFICE
CERTIFICATE OF CORRECTION

PATENT NO. : 12,115,263 B2  
APPLICATION NO. : 17/183318  
DATED : October 15, 2024  
INVENTOR(S) : Vulcu et al.

Page 1 of 1

It is certified that error appears in the above-identified patent and that said Letters Patent is hereby corrected as shown below:

In the Specification

Column 2, Line 66, change ""off" position" to -- "on" position --

In the Claims

Column 6, Line 58, Claim 11, change "electric" to -- electrical --

Signed and Sealed this  
Twenty-sixth Day of November, 2024

Katherine Kelly Vidal  
*Director of the United States Patent and Trademark Office*